United States Patent [19]
Patil et al.

[11] Patent Number: 5,696,286
[45] Date of Patent: Dec. 9, 1997

[54] PROCESS FOR THE PREPARATION OF AROMATIC-SUBSTITUTED ALIPHATIC CARBOXYLIC ACIDS

[75] Inventors: Deepak R. Patil, Orangeburg; George A. Knesel, Columbia; Patricia Pringle, Pinewood, all of S.C.

[73] Assignee: Albemarle Corporation, Richmond, Va.

[21] Appl. No.: 109,861

[22] Filed: Aug. 9, 1993

Related U.S. Application Data

[63] Continuation of Ser. No. 724,167, Jul. 1, 1991, abandoned.
[51] Int. Cl.$^6$ .................................................. C07C 53/134
[52] U.S. Cl. ............................................................. 562/496
[58] Field of Search ............................................. 562/496

[56] References Cited

U.S. PATENT DOCUMENTS 4,952,718  8/1990  Stahly ............................ 558/388

FOREIGN PATENT DOCUMENTS 0074174  5/1952  Denmark .

*Primary Examiner*—Joseph Conrad
*Attorney, Agent, or Firm*—Philip M. Pippenger

[57] ABSTRACT

A process for the preparation of aromatic substituted carboxylic acids is disclosed. The process comprises
i) forming an aromatic-substituted acrylonitrile by dehydrating a cyanohydrin of the formula

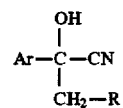

where Ar is $C_6$ to $C_{10}$ aryl unsubstituted or substituted with $C_1$ to $C_6$ linear or branched alkyl, $C_1$ to $C_6$ linear or branched alkoxy, halo, amino, amino mono- or disubstituted with $C_1$ to $C_6$ linear or branched alkyl or carboxylic acid or the alkyl esters thereof; and R is hydrogen or $C_1$ to $C_6$ linear or branched alkyl;

ii) catalytically reducing the aromatic-substituted acrylonitrile when not more than 10% of the cyanohydrin is converted to said acrylonitrile to form a first reaction solution comprising an aromatic substituted aliphatic nitrile;

iii) hydrolyzing the aromatic-substituted aliphatic nitrile.

This process is useful in the preparation of compounds that are intermediates for physiologically active aromatic substituted acetic acids similar to the profen-type compounds.

20 Claims, No Drawings

PROCESS FOR THE PREPARATION OF AROMATIC-SUBSTITUTED ALIPHATIC CARBOXYLIC ACIDS

This is a continuation of application Ser. No. 07/724,167 filed on Jul. 1, 1991, now abandoned.

FIELD OF INVENTION

This invention relates to a process for preparing aromatic-substituted aliphatic carboxylic acids. More particularly, this invention relates to a process for preparing aromatic substituted aliphatic carboxylic acids by the dehydration of an aromatic-substituted cyanohydrin and subsequent reduction of the resulting acrylonitrile.

BACKGROUND OF THE INVENTION

The preparation of carboxylic acids by the hydrolysis of nitriles is a well recognized reaction. It typically is carried out with either acid or base catalysis.

Cyanohydrins similarly produce carboxylic acids upon hydrolysis. However, these hydrolytically produced acids are substituted at the α-carbon with a hydroxyl group. Aliphatic cyanohydrins of this type are relatively stable. However, cyanohydrins having aromatic substituents do not lend themselves to such processes. These cyanohydrin substrates are unstable to hydrolytic conditions, initially dehydrating and then continuing to react to produce dimers. Further reaction to produce the fully saturated carboxylic acids is therefore not possible in high yield.

It is therefore an object of the present invention to provide a method for producing aromatic substituted aliphatic carboxylic acids.

It is a further object of this invention to provide method for treating aromatic-substituted cyanohydrins to form aromatic-substituted aliphatic carboxylic acids.

These and other objects of the present invention will appear from the description of the preferred embodiments as set forth below.

DESCRIPTION OF THE PREFERRED EMBODIMENTS

The process of the present invention requires as a first step the dehydration of a cyanohydrin of the formula

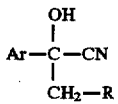

where Ar is $C_6$ to $C_{10}$ aryl unsubstituted or substituted with $C_1$ to $C_6$ linear or branched alkyl, $C_1$ to $C_6$ linear or branched alkoxy, halo, amino, amino mono- or disubstituted with $C_1$ to $C_6$ linear or branched alkyl or carboxylic acid or the alkyl esters thereof; and R is hydrogen or $C_1$ to $C_6$ linear or branched alkyl.

The dehydration produces aromatic substituted acrylonitriles of the formula

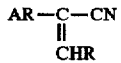

where Ar and R are as previously defined.

In the dehydration process, it is preferred that Ar is phenyl unsubstituted or substituted with $C_1$ to $C_6$ linear or branched alkyl, $C_1$ to $C_6$ linear or branched alkoxy, halo or carboxylic acid or alkyl esters thereof, most preferably the methyl, ethyl or isobutyl alkyl esters. Preferably R is hydrogen or $C_1$ to $C_6$ linear or branched alkyl, most preferably hydrogen.

As noted above, the dehydration process produces unsaturated nitriles having aromatic substitution. Typically, these aromatic substituted unsaturated nitriles display some measure of instability and readily dimerize or polymerize to unwanted and, in many cases, intractable higher molecular weight compounds. However, it has been found that such further, undesired reaction can be inhibited by carrying out the dehydration so that the amount of unsaturated nitrile formed in the first reaction solution (the solution produced from the combination of the cyanohydrin, the unsaturated nitrile and small amounts of dehydrating agent) does not exceed about 10% of the theoretical amount based on the quantity of cyanohydrin that disappears during the dehydration reaction. As a result, the (first) reaction solution comprises mostly unreacted cyanohydrin starting material and lesser amounts of aromatic-substituted unsaturated nitrile.

In order to further prevent the destruction of the unsaturated material produced in the dehydration reaction, the temperature of the reaction should not be permitted to exceed about 90° C. Temperatures below about 40° C. are not advantageous since dehydration rates diminish disadvantageously. Preferably, the dehydration is carried out between about 50° C. to about 70° C.

A variety of organic and inorganic (mineral) acids can be used as the dehydrating agent in the process of the present invention. However, it has been found that acids having negative pKa's are preferred. Since the presence of water shifts the dehydration equilibrium disadvantageously to the left, these acids having negative pKa's should be substantially anhydrous. Thus, mineral acids such as phosphoric, sulfuric, hydrobromic, etc., are effective as dehydrating agents herein and are preferred. Organic acids, such as p-toluenesulfonic, benzene sulfonic, etc., are also useful in the dehydration process of the present invention. Particularly preferred is 90% phosphoric acid.

As noted above, the result of the dehydration step in accordance with the preferred embodiment of the present invention is a first reaction solution containing mostly unreacted cyanohydrin and smaller amounts of unsaturated nitrile. It is this first reaction solution that is used as the starting materials for the second, catalytic reduction step.

The reduction utilizes the generally accepted metallic or organometallic materials known in the prior art as effective in catalytic hydrogenations. Thus, noble metal catalysts such as palladium, ruthenium, platinum either supported or unsupported are useful reducing agents for the hydrogenation step of the present process. Hydrogen is typically supplied to the reaction vessel and the reaction mixture maintained under hydrogen pressure, usually about 50 to 100 psig. Preferably, the catalytic reduction is carried out with palladium supported on carbon at a temperature of from about 25° C. to about 90° C., preferably 40° C. to 70° C.

The alkali metal hydrides, which provide their own source of hydrogen, are also effective herein.

In one embodiment of the present invention, the reaction mixture formed from the catalytic hydrogenation step is subject to hydrolysis, typically with an aqueous alkali solution, which hydrolyzes the nitrile in accordance with the following equation

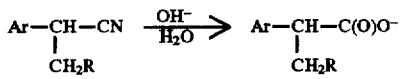

The hydrolysis of nitriles is well known. See, for example, March, *Advanced Organic Chemistry*, 3d Edition, 1985, page 788, incorporated herein by reference.

In another embodiment of the present invention, the reaction mixture formed from the catalytic hydrogenation step is again treated with a dehydrating agent in the manner disclosed herein as the first step of the process of the present invention, thus forming a second reaction solution. Again, the process is halted when the amount of unsaturated nitrile produced from the dehydration of the cyanohydrin does not exceed 10% of the theoretical amount based on the quantity of cyanohydrin that disappears during the dehydration reaction.

Catalytic hydrogenation of the second reaction solution produces a reaction mixture having almost twice the amount of aromatic substituted aliphatic carboxylic acid as was present after the first reaction-sequence. Obviously, multiple repetitions of steps i) and ii) will ultimately result in a product stream that is substantially completely almost all aromatic-substituted aliphatic carboxylic acid. Since reaction steps i) and ii) are relatively rapid (a few minutes for each step), a product stream of almost 100% saturated carboxylic acid resulting from the final hydrolysis step occurs in a relatively short time.

The following examples are used herein for the purposes of illustration only. They should not be regarded as limiting the invention as set forth by the claims appended hereto in any way.

EXAMPLES

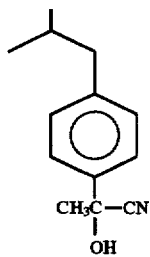

I

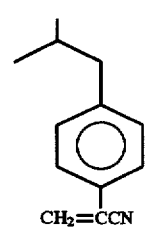

II

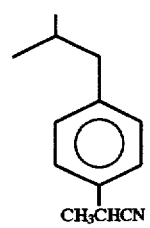

III

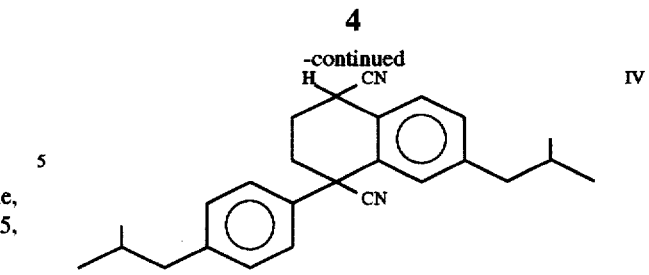

IV

Example 1

Dehydration of p-Isobutylacetophenone Cyanohydrin

A 500 mL 3-neck round bottom flask, equipped with an agitator, a Dean and Stark trap to remove water, and an addition funnel, was charged with 25 g of 85% phosphoric acid and 100 g of hexane. The reactor was heated to 72° C. with reflux. From the addition funnel, 104 g of I was added over a three hour period and the reaction was continued for another two hours. Gas chromatography showed a 97% conversion of I, with a 57% yield of II, and 14% yield of dimer, IV.

Example 2

Hydrogenation of α-(p-isobutylphenyl)acrylonitrile, II

The reaction mass from Example 1 was charged to a 450 mL autoclave along with 3 g of 5% Pd/C. The autoclave was heated to 75° C. and pressured to 50 psig with hydrogen. After 25 minutes, there was a 75% conversion of II to III.

We claim:

1. Process for preparing an aromatic substituted aliphatic carboxylic acid which comprises i) forming an aromatic-substituted acrylonitrile by treating a cyanohydrin of the formula

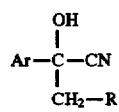

where Ar is $C_6$ to $C_{10}$ aryl unsubstituted or substituted with $C_1$ to $C_6$ linear or branched alkyl, $C_1$ to $C_6$ linear or branched alkoxy, halo, amino, amino mono- or disubstituted with $C_1$ to $C_6$ linear or branched alkyl or carboxylic acid or the alkyl esters thereof; and R is hydrogen or $C_1$ to $C_6$ linear or branched alkyl with a dehydrating agent;

ii) catalytically reducing the aromatic-substituted acrylonitrile when not more than 10% of the cyanohydrin is converted to said acrylonitrile to form a first reaction mixture comprising an aromatic substituted aliphatic nitrile;

iii) treating said first reaction mixture with a dehydrating agent according to step i) to form said aromatic-substituted acrylonitrile;

iv) catalytically reducing the aromatic-substituted acrylonitrile when not more than 10% of the cyanohydrin is converted to said acrylonitrile according to step ii) to form a second reaction solution comprising said aromatic substituted aliphatic nitrile; and v) hydrolyzing the aromatic-substituted aliphatic nitrile produced in steps ii) and iv).

2. The process according to claim 1 wherein Ar is phenyl unsubstituted or substituted with $C_1$ to $C_6$ linear or branched alkyl, $C_1$ to $C_6$ linear or branched alkoxy, halo or carboxylic acid or the alkyl esters thereof.

3. The process according to claim 2 wherein R is hydrogen or $C_1$ to $C_3$ linear or branched alkyl.

4. The process according to claim 1 wherein said dehydrating is carried out at a temperature of from about 40° C. to about 90° C.

5. The process according to claim 4 wherein said dehydrating is carried out with an acid having a negative pKa.

6. The process according to claim 5 wherein said acid is a mineral acid.

7. The process according to claim 6 wherein said acid is phosphoric acid.

8. The process according to claim 1 wherein said catalytic reducing is carried out at a temperature of from about 40° C. to about 90° C. and a pressure of about 50 psi to about 100 psi.

9. The process according to claim 8 wherein the said catalytic reducing is carried out using palladium or carbon as the catalyst.

10. The process according to claim 1 wherein said i) and ii) are repeated until substantially all of said cyanohydrin has been dehydrated according to step i) and the acrylonitrile catalytically reduced according to step ii).

11. A process for preparing a phenyl substituted aliphatic carboxylic acid which comprises i) forming a phenyl-substituted acrylonitrile by treating a cyanohydrin of the formula

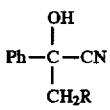

wherein Ph is phenyl unsubstituted or substituted with $C_1$ to $C_6$ linear or branched alkyl, $C_1$ to $C_6$ linear or branched alkoxy, halo, amino, amino mono- or disubstituted with $C_1$ to $C_6$ linear or branched alkyl or carboxylic acid or the alkyl esters thereof; and R is hydrogen or $C_1$ to $C_6$ linear or branched alkyl with a dehydrating agent;

ii) catalytically reducing said phenyl-substituted acrylonitrile when not more than 10% of the cyanohydrin is converted to said acrylonitrile to form a first reaction mixture comprising phenyl substituted aliphatic nitrile;

iii) treating said first reaction mixture with a dehydrating agent according to step i) to form said phenyl-substituted acrylonitrile;

iv) catalytically reducing the phenyl-substituted acrylonitrile when not more than 10% of the cyanohydrin is converted to said acrylonitrile according to step ii) to form a second reaction solution comprising said phenyl-substituted aliphatic nitrile; and v) hydrolyzing the phenyl-substituted aliphatic nitrile.

12. The process according to claim 11 wherein said phenyl is unsubstituted or substituted with $C_1$ to $C_6$ linear or branched alkyl, $C_1$ to $C_6$ linear or branched alkoxy, halo or carboxylic acid or the alkyl esters thereof.

13. The process according to claim 12 wherein R is hydrogen or $C_1$ to $C_3$ linear or branched alkyl.

14. The process according to claim 11 wherein said dehydrating is carried out at a temperature of from about 40° C. to about 90° C.

15. The process according to claim 14 wherein said dehydrating is carried out with an acid having a negative pKa.

16. The process according to claim 15 wherein said acid is a mineral acid.

17. The process according to claim 16 wherein said acid is phosphoric acid.

18. The process according to claim 11 wherein said catalytic reducing is carried out at a temperature of from about 40° C. to about 90° C. and a pressure of about 50 psi to about 100 psi.

19. The process according to claim 18 wherein the said catalytic reducing is carried out using palladium as the catalyst.

20. The process according to claim 11 wherein said i) and ii) are repeated until substantially all of said cyanohydrin has been dehydrated according to step i) and the acrylonitrile catalytically reduced according to step ii).

* * * * *